(12) United States Patent
Weber et al.

(10) Patent No.: US 6,629,932 B2
(45) Date of Patent: Oct. 7, 2003

(54) ALLERGEN AND IRRITANT MEASURING DEVICE

(75) Inventors: Paul J. Weber, Ft. Lauderdale, FL (US); Kenneth B. Trauner, Sacramento, CA (US); Luiz B. Da Silva, Danville, CA (US)

(73) Assignee: Pearl Technology Holdings, LLC, Tampa, FL (US)

( * ) Notice: Subject to any disclaimer, the term of this patent is extended or adjusted under 35 U.S.C. 154(b) by 185 days.

(21) Appl. No.: 09/758,400

(22) Filed: Jan. 10, 2001

(65) Prior Publication Data

US 2002/0091334 A1 Jul. 11, 2002

(51) Int. Cl.[7] .................................................. A61B 5/08
(52) U.S. Cl. ....................... 600/529; 600/549; 600/556; 600/388; 600/389; 600/390
(58) Field of Search ................................. 600/529, 549, 600/556, 474, 493, 479, 537, 538, 545, 584, 388, 389, 390; 604/20, 385.01

(56) References Cited

U.S. PATENT DOCUMENTS

| | | | | |
|---|---|---|---|---|
| 4,164,937 A | * | 8/1979 | Spencer | 600/479 |
| 4,397,317 A | * | 8/1983 | Villa-Real | 600/493 |
| 4,809,707 A | * | 3/1989 | Kraft et al. | 600/549 |
| 4,819,657 A | * | 4/1989 | Kraft et al. | 600/549 |
| 4,945,919 A | * | 8/1990 | Hattori | 600/549 |
| 5,373,851 A | * | 12/1994 | Reinhold, Jr. et al. | 600/529 |
| 5,413,111 A | * | 5/1995 | Wilkinson | 600/537 |
| 5,817,012 A | * | 10/1998 | Schoendorfer | 600/584 |
| 6,289,240 B1 | * | 9/2001 | Weber et al. | 600/545 |
| 6,433,244 B1 | * | 8/2002 | Roe et al. | 604/385.01 |

* cited by examiner

Primary Examiner—Teresa Walberg
Assistant Examiner—Fadi H. Dahbour
(74) Attorney, Agent, or Firm—John P. Wooldridge

(57) ABSTRACT

A device is described that can be easily used to warn an asthmatic or allergen reacting patient of irritant levels which may trigger an asthma or allergy attack for that person. The device continually monitors and records irritants in the air, and when the concentration exceeds the predefined level the device generates an alarm signal for the user. The recorded data can be downloaded to a computer, and this information can be used by the patient and the physician to identify irritants, guide treatment, and determine threshold levels.

42 Claims, 3 Drawing Sheets

ALLERGEN AND IRRITANT MEASURING DEVICE

BACKGROUND OF THE INVENTION

1. Field of the Invention

The present invention relates to a device and method to monitor irritants and allergens in the air that can induce/trigger an asthmatic and/or allergic reaction. The device is carried by the patient and continuously monitors and records irritants in the air. When the concentration of irritant or allergen in the air exceeds a predefined level, the device generates a signal for the user. The causative factor concentration is continuously monitored and available for downloading into a computer. This information can be used by the patient and physician to identify irritants, guide therapy or modify threshold levels.

2. Description of Related Art

Asthma is a chronic breathing disease. During an asthma attack airflow to the lungs is restricted making breathing difficult and potentially life threatening. Airflow may be restricted due to constriction of the muscles around the airway, inflammation and swelling of the airway, or increased production of mucus that clogs the airway. The severity of asthma varies from person to person; some people must take medication on a daily basis while others need only take medication when they have symptoms of asthma. The primary symptoms of asthma include coughing, wheezing or whistling when breathing, shortness of breath, tightness in the chest, and congestion.

Asthma can be an inherited condition. In most young people asthma is caused by an allergy. Asthma can also be caused by exercise, cold air, tobacco smoke, emotional stress, infections, some drugs (e.g., beta blockers), laughing, irritants in asthma inhalers, breathing tests, sulfur dioxide, gastro-esophageal reflux, histamine or methacholine aerosols. Some people experience occupational asthma that is caused by dust or fumes produced on the job (e.g., flour, soldering by-products, polyurethane paints, plastic molding, epoxy resin molding, phthalates in paints, wood dust, textile dyes, animal work by-products, pharmaceutical industry by-products, platinum refining by-products, enzymes in washing detergents).

For purposes of this application, an irritant is defined as typically a simple molecule with direct toxic potential, e.g., soldering fumes. For purposes of this application, an allergen is defined as typically a complex protein or carbohydrate, animal or plant component that attaches to immune cells for recognition, e.g., cat saliva on its dander.

Currently, there is no cure for asthma, but there are steps that can be taken to lessen the effects that asthma has on a person's life. Common environmental "triggers" frequently cause asthma attacks. Asthmatics need to be observant of their surroundings when having an attack in order to determine and become aware of the triggers that induce an asthma attack. Some triggers that can cause an asthma attack are smoke, pets, pet hair and dander, pollen or grass, dust, mold, excessive physical activity, cockroaches, cold air, certain weather conditions, laughing, yelling, crying, strong odors, chemicals, sprays and aerosols (e.g., hairspray), and viral infections (e.g., colds, pneumonia, bronchitis). An asthma attack can vary from mild to severe. It is important to recognize symptoms early in order to administer appropriate treatment and avoid a severe attack.

Medications are used to control asthma. Inhaled medications are used to relax the muscular wall of the airways and make breathing easier. Bronchodialators are used to relieve constricted airways. A machine called a nebulizer may be used by some patients to administer liquid medication as a mist. Another means of delivering liquid medication in a mist form is a small device called a metered dose inhaler (MDI).

Asthma can be controlled by taking medications as directed by the physician, daily monitoring of lung function (use of peak flow meter), recognizing early warning signs of an attack, monitoring living environments to avoid triggers, and the proper use of all medical equipment necessary for asthma treatment. The best way to avoid an asthma attack is to monitor and avoid those triggers that cause an attack in an individual.

There is a need for a device that monitors irritants in the air that can trigger an asthmatic, allergic, or bronchitic reaction. The present invention fulfills this need, and further provides related advantages.

SUMMARY OF THE INVENTION

An object of the present invention is to provide a device and method to monitor irritants and/or allergens in the air that can trigger an asthmatic or allergic reaction.

The device may be carried by the patient and continuously monitors and records irritants or allergens in the air. When the concentration of either in the air exceeds a predefined level the device generates a signal for the user. The irritant or allergen concentration is continuously monitored and available for downloading into a computer. This information can be used by the patient and physician to identify irritants, guide therapy or modify threshold levels.

An embodiment of the present invention is a small battery powered device to be worn by a patient. For example, it may be worn outside the clothes and attached to the waistband by a clip. The device could also be placed in home or office near the patient. The device consists of a measuring device, an LCD display, a sampling port, a sensor module, and input buttons. The best way to avoid these types of rapid respiratory born illnesses is to monitor and avoid those triggers that cause such an attack in an individual. The sensor module in the present invention is disposable and can be tailored to monitor irritants and allergens that may trigger a reaction for that individual. The sensor module in the device can contain more than one detection stage and input filter in order to improve particle size analysis and identification. The device can also include gas sensors and a temperature sensor. This information can be recorded and used for later analysis. By operating the buttons on the device, the user can control the device and specify the irritants or allergens and levels to be measured. The LCD display shows the irritant levels and sounds an alarm (either acoustic or vibration or light) to warn the user when the threshold has been met and a possible asthma attack or other respiratory reaction could occur.

Within the present invention is a microprocessor and memory that control the operation of the device. The control electronics allow data to be exchanged between the sensors and the microprocessor. The analyzed data is displayed on the LCD display. The measuring device is controlled by the individual as to his specific triggers and alarm conditions. The device is also capable of transmitting collected data, by wireless communication or direct connection to a remote computer, all of the sensor measurements collected during the day. This information can be used by the patient and physician to identify irritants, guide treatment, and set threshold levels.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is a device and method for monitoring irritants or allergens in the air that can trigger an acute or subacute respiratory illness or reaction. The portable and compact device may be carried by the patient to continuously monitor and record irritants in the air. The device will generate a signal for the user when the concentration of irritants or allergens in the air exceeds a predefined level. The invention provides a means for downloading irritant or allergen concentration levels into a computer. The patient and physician are thus enabled to use the irritant concentration levels to identify defined or suspected irritants or allergens, guide therapy or modify threshold levels.

Figure 1:
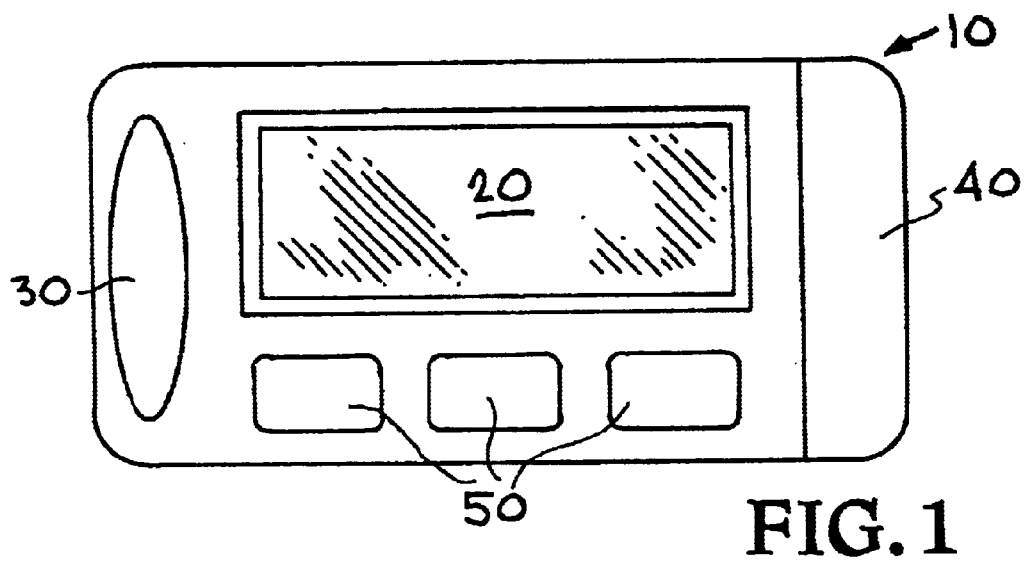
FIG. 1 is an illustration of the measuring device.

FIG. 1 is an illustration of the outside of the device. The measuring device 10 includes an LCD display 20, a sampling port 30, a sensor module 40 and input buttons 50. The patient activates and controls operation of the device 10 by operating buttons 50. User controlled functions include method of signaling an alarm, e.g., vibration, acoustic and/or light signal. For each irritant measured, the patient may also specify the threshold level to signal an alarm. The LCD display 20 shows status, control menus and can display the current irritant levels. The disposable sensor module 40 contains a variety of irritant and gas sensors. The sensors included in the module 40 can be tailored to the specific patient. The measuring device 10 is battery powered and is carried by the user such that clothes do not obscure the sampling port 30. In one embodiment, the device is attached to the waist belt by a clip with the sampling port 30 facing away from the user. A miniature fan or pump within the device draws air through the sampling port and into the sensor module 40. Small fans are now possible using microelectromechanical systems (MEMS) technology. (see e.g., http://www.cfdrc.com/datab/Applications/MEMS/mems.html (Gerlach and Wurmus, *Sensors and Actuators A*, Vol. 50, 1995).

Figure 2:
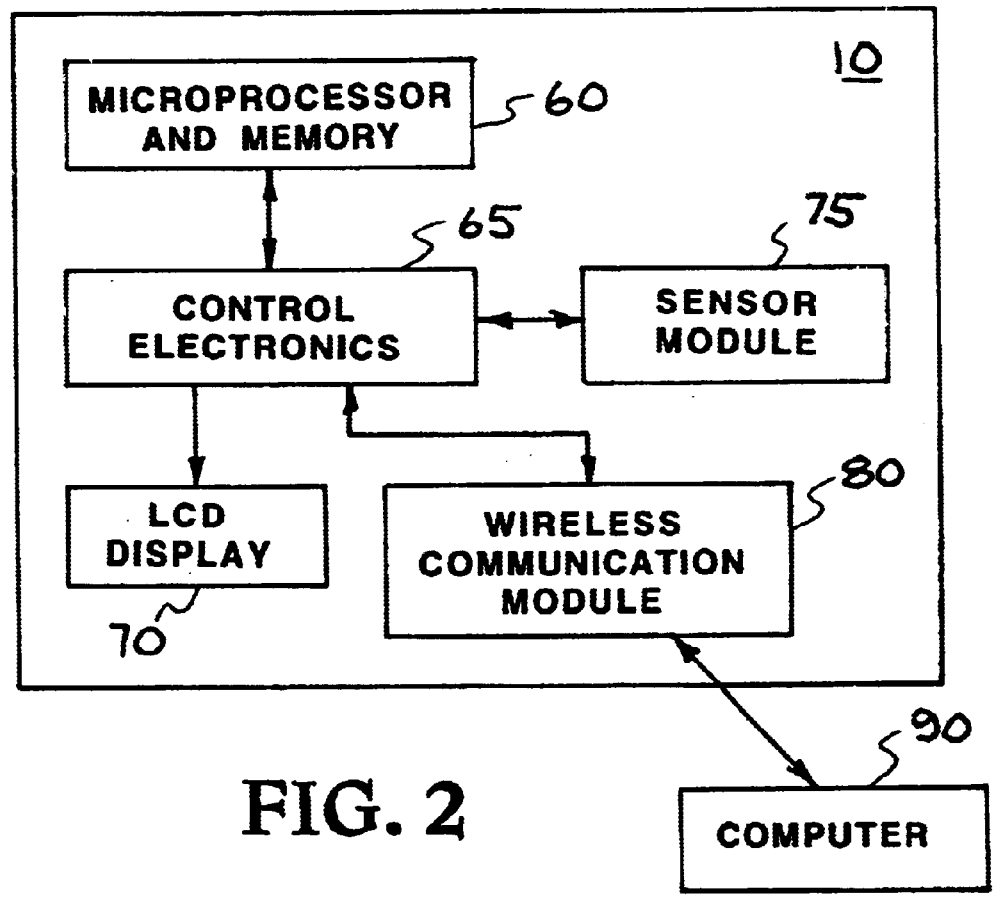
FIG. 2 is a block diagram of the key components of the device.
Figure 3:
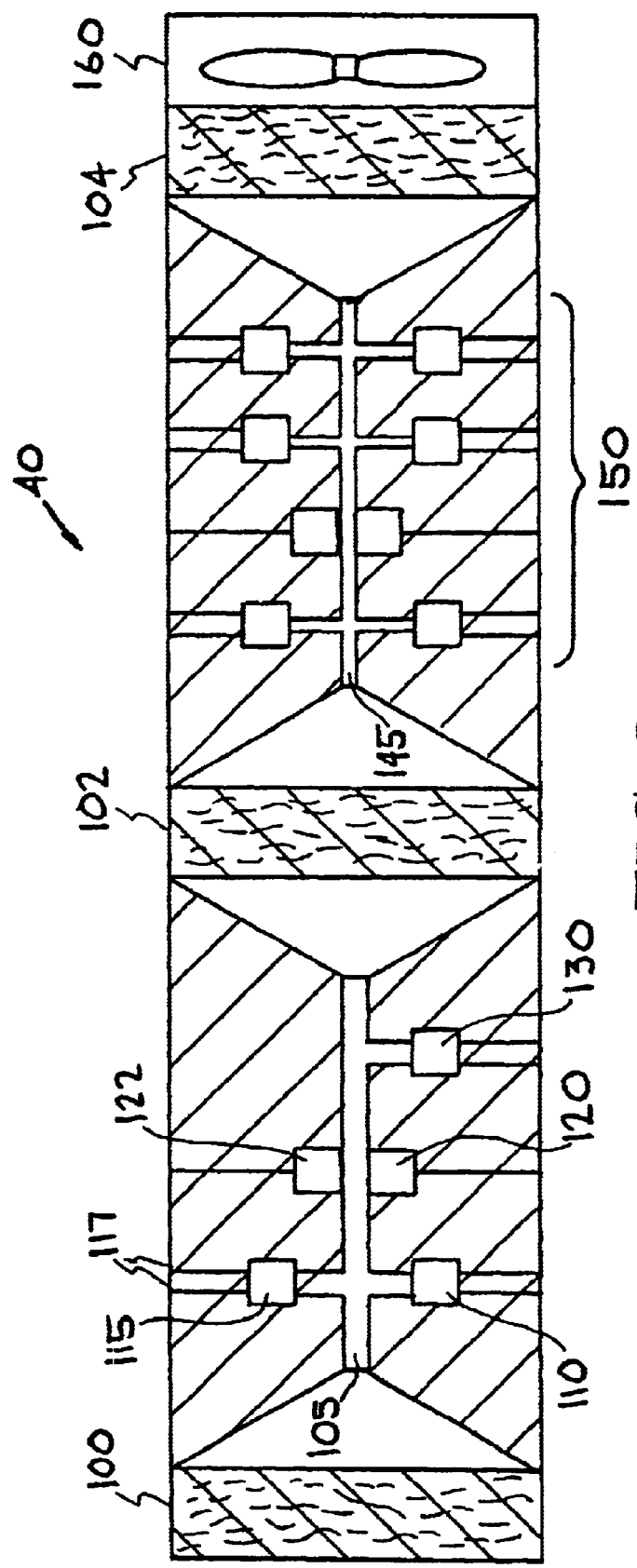
FIG. 3 shows a sectional view of one embodiment of the sensor module used in the device.

FIG. 2 shows a block diagram of the key components of the measuring device 10. A microprocessor and memory 60 control operation of the device. Control electronics 65 exchange data between the sensor module 75 and the microprocessor 60 that analyzes the data and displays readings on the LCD display 70. Patient input to the microprocessor is used to control operation and specify alarm conditions. In addition, the user can command the device 10 to transmit, using a wireless communication module 80 to a remote computer 90, a log of all sensor measurements collected during the day. The wireless communication module 80 could use simple RF communication or technology now available such as the Blue Tooth chip set FIG. 3 shows a cross sectional view through one embodiment of the sensor module 40. The sensor module consists of at least one detection stage and an input filter. Air is drawn by a miniature fan 160 into the detection section through input filter 100. The input air particle filter 100 eliminates all large particles (or irritants) that could block the micro capillary 105. Suitable particle filters for the first stage block all particles greater than 300 micron in size. Usable filter materials include cotton, micropore ceramic, paper, polymer, foam, zeolite, and activated carbon. Once particles enter the micro capillary 105, they flow past one or more sensors that measure properties of the particles. In the embodiment shown in FIG. 3 the first sensor consists of a light source 110 that shines light through the micro capillary to an optical detector 115. Suitable miniature light sources are light emitting diodes, which can operate at wavelengths ranging from 370 nm to 1300 nm. The LEDs can be coupled to fiber optics with optional GRIN lenses that direct the light through the capillary. The optical detector 115 is powered through electrical wires 117 and measures the light transmitted through the micro capillary 105. The optical detector 115 can be filtered to reduce any background light. An additional optical detector positioned at approximately 90 degrees to light source 110 detects side scattered light. The amount of side scattered light can be used to estimate the size of the particles. The second sensor consists of two electrodes 120 and 122 that measure the impedance of the particles as they flow by. The electrical impedance of particles is sensitive to the molecular structure and particle size, making the electrical impedance a valuable diagnostic to identify particle type. Multiple electrical impedance sensors that measure properties at different frequencies can be incorporated into each detection module. Alternatively, by driving the electrodes with a multifrequency signal, each impedance sensor can make measurements at multiple frequencies simultaneously. A third sensor is a fluorescence sensor and consists of an optical excitation source 130 and a filtered optical detector (in plane not shown) that detects the emitted fluorescence.

The sensor module 40 shown in FIG. 3 includes a second filter 102 and second detection stage 150 that allows more sensitive detection of small particles. The second detection stage can be identical to the first except that it has a smaller micro capillary. Alternatively, the second detection stage can include additional optical and electrical sensors that are more specific to the smaller particles. Additional detection stages can be added to further improve particle size analysis and identification. A final filter 104 may be included that filters the air before exiting the device to collect all particles greater than 0.1 micron. This is valuable because the sensor module can be removed from the device and analyzed in a laboratory for additional particle and allergen analysis. A miniature fan or air pump 160 draws air through the sensor modules. A second fan or air pump could also be placed at the front of the sensor modules to provide to increase air flow.

For asthmas, the largest irritants/allergens may have mites and pollens that can be hundreds of microns in size. The smallest particle irritants can be pollutants in the air that can be as small as a fraction of a micron. In one embodiment, the first filter 100 allows particles smaller than 300 micron to flow through and into the micro capillary channel 105 and the second filter 102 allows particle smaller than 25 microns to flow through and into the micro capillary channel 145.

The size of the micro capillaries 105 and 145 may be 300 microns and 50 microns respectively.

Although the described sensor module incorporates the light source and detector into the module itself, an alternative embodiment would have the light source and detector in the device. In this embodiment lenses could be used to couple the light through the capillary and collect it into the detectors. In addition to particle sensing the sensor module could include gas sensors to measure the concentration of oxygen, nitrogen, $CO_2$, CO, NO, $NO_2$, Ozone. A temperature sensor could also be integrated into the device and the temperature recorded into memory for later analysis.

Each sensor module includes a means to identify the type of sensors used by that module. The module identification means could be a simple electrical connection that connects to a different pin depending on sensor type. Alternatively, it could be a bar code on the sensor module.

Figure 4:
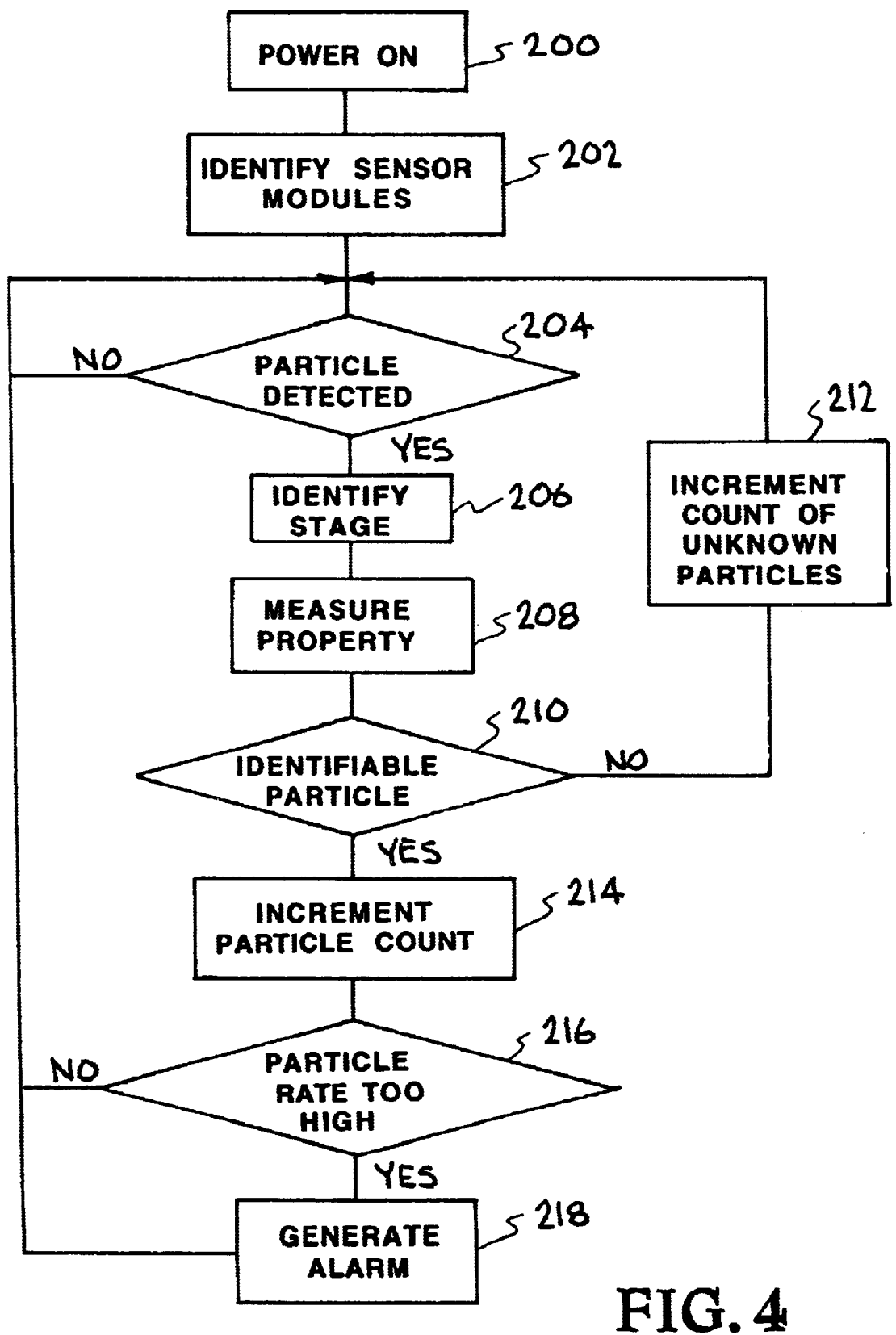
FIG. 4 shows a flow chart for the main control software routine.

FIG. 4 shows a flow chart for the main control subroutine. After power has been turned on (200), the microprocessor communicates with the control electronics to identify (202) the type of sensor modules currently loaded. When a particle is detected (204), the program records which sensor module and stage detects the particle (206). This information is used to monitor particle movement and track particle loss. The optical and electronic properties of the particle are measured (208) as the particle moves through the sensor module. When all the properties have been measured and a particle has been identified (210) the results are compared to a table of known particles. If no match exists the program increments the count (212) of unknown particles and optionally the measured properties for later downloading. If the measured properties are within a predefined range for a know particle, the particle is identified and the count for that particle type incremented (214). If the particle rate is above the user specified threshold (216) the device generates an alarm (218) to notify the user. If the particle rate is below the threshold, the program returns to the particle detection step (204).

In one embodiment, all the sensor data measured by the device can be downloaded into a computer where it can be stored for future analysis. This data can then be used by physician or patient to identify what sequence of events might have triggered the allergic or asthmatic reaction. This information can then be used to modify the threshold values to generate an alarm at a more appropriate value. One embodiment of the invention allows the user to download information from a portable respiratory testing apparatus that demonstrates bronchospasms such as by recording Forced Expiratory Volume in one second (FEVI) values. This will quantify a decrease in pulmonary function and correlate to the presence of an antigen/irritant. Bronchoprovocation tests currently exist for which there are reimbursement codes. Coupling a portable FEVI testing device to the present invention will allow physicians to charge for bronchoprovocation testing. Use of a FEVI device combined with temperature and antigen exposure will also allow the device to address Exercise Induced Asthma (EIA).

There are innumerable allergens of multiple different classes and vaccines have been produced for many of these. Pollens include the tree, weed and grass pollens. Domestic animals and rodents produce characteristic antigens. Several genera of mites have been found to cause allergies. Insects can cause sting or bite allergies as well as inhalant allergies. Several fungal species, usually molds, cause allergic reactions.

Occupational asthma refers to asthma associated with industrial exposures and is a large area in workers compensation and a large economic concern to employers. Many of the occupational irritants are gases that the present invention can detect. Occupational agents that can cause asthma include high-molecular-weight agents, such as natural proteins, and low-molecular-weight chemicals, such as diisocyanates. Occupational chemicals implicated in workplace asthma include anhydrides, antibiotics, diisocyanates, wood dust and dyes. High-molecular-weight allergens are usually derived from plant and animal proteins. There are numerous proteins implicated in occupational asthma. Among those most commonly encountered are vegetable gums, enzymes, animal proteins, insects, plant proteins, and lgumes. See "ALLERGY Theory and Practice"Second Edition, (1992) by Korenblat and Wedner, ISBN 0-7216-7244-2. See also "ALLERGY Principles and Practice" (1993) by Elliott Middleton, Jr., MD et al., ISBN 0-8016-6427-6. See also "Diagnostic Testing of Allergic Disease" (2000) by Kemp and Lockley, ISBN 0-8247-0303-0.

The above descriptions and illustrations are only by way of example and are not to be taken as limiting the invention in any manner. One skilled in the art can substitute known equivalents for the structures and means described. The full scope and definition of the invention, therefore, is set forth in the following claims.

We claim:

1. An apparatus, comprising:
   control electronics;
   at least one sensor for detecting at least one type of particle selected from the group consisting of an allergen and an irritant, wherein said sensor is operatively connected to said control electronics, wherein said sensor produces data when it detects said at least one type of particle;
   a microprocessor and memory operatively connected to said control electronics, wherein said control electronics can communicate said data from said sensor to said microprocessor, wherein said microprocessor comprises software that can analyze said data to produce analyzed data; and
   a display operatively connected to said control electronics.

2. The apparatus of claim 1, wherein said control electronics communicates information to said display.

3. The apparatus of claim 2, wherein said information is selected from the group consisting of said data, said analyzed data, an apparatus menu and apparatus status.

4. The apparatus of claim 1, wherein said display comprises a liquid crystal display.

5. The apparatus of claim 1, wherein said software can quantify said at least one type of particle.

6. The apparatus of claim 1, further comprising a fan operatively connected to draw ambient particles into said sensor.

7. The apparatus of claim 1, wherein said at least one sensor comprises at least one detector.

8. The apparatus of claim 1, wherein at least one element selected from the group consisting of said sensor, said control electronics, said microprocessor and memory and said display are battery powered.

9. The apparatus of claim 1, wherein said at least one sensor is selected from the group consisting of a gas sensor, a temperature sensor, an optical sensor, a fluorescence sensor and an electrical impedance sensor.

10. The apparatus of claim 1, wherein said at least one sensor is selected from the group consisting of an allergen sensor and an irritant sensor.

11. The apparatus of claim 1, wherein said software comprises means for specifying the irritants or allergens and their levels to be measured.

12. The apparatus of claim 1, further comprising means for generating a signal when the concentration of said at least one particle exceeds a predefined level.

13. The apparatus of claim 12, wherein said signal is selected from the group consisting of an acoustic signal, a vibration signal and a light signal.

14. The apparatus of claim 1, further comprising a wireless communication module operatively connected to said control electronics, wherein said wireless communication module is capable of transmitting said data and said analyzed data to a remote computer.

15. The apparatus of claim 14, wherein said wireless communication module comprises a wireless information transmitting mechanism selected from the group consisting of RE communication technology and Blue Tooth communication technology.

16. The apparatus of claim 1, further comprising means for attaching said apparatus to a patient.

17. The apparatus of claim 1, further comprising means for attaching said apparatus in a home or an office.

18. The apparatus of claim 1, wherein said at least one sensor is disposable.

19. The apparatus of claim 1, further comprising an input filter.

20. The apparatus of claim 19, wherein said input filter comprises filter material selected from the group consisting of cotton, micropore ceramic, paper, polymer, foam, zeolite and activated carbon.

21. The apparatus of claim 1, wherein said at least one sensor comprises at least one light source directed onto at least one optical detector.

22. The apparatus of claim 21, wherein said at least one light source comprises a light emitting diode (LED).

23. The apparatus of claim 22, wherein said LED can operate at wavelengths ranging from 370 nm to 1300 nm.

24. The apparatus of claim 21, further comprising at least one optical filter operatively placed to filter undesired light from said at least one optical detector.

25. The apparatus of claim 21, further comprising at least one additional optical detector positioned at approximately 90 degrees to said at least one light source to detect scattered light.

26. The apparatus of claim 25, wherein the amount of said scattered light is used to estimate the size of said at least one particle.

27. The apparatus of claim 1, wherein said at least one sensor comprises at least one electrical impedance sensor comprising two electrodes that use at least one frequency to measure the impedance of said at least one particle as it flows by.

28. The apparatus of claim 27, wherein said at least one electrical impedance sensor comprises a plurality of impedance sensors each configured to measure impedance at different frequencies.

29. The apparatus of claim 1, wherein said at least one sensor comprises at least one fluorescence sensor comprising at least one optical excitation source and at least one optical detector for detecting fluorescence emitted by said at least one particle.

30. The apparatus of claim 29, wherein said at least one fluorescence sensor comprises a plurality of fluorescence sensors each having sensitivity to different particles.

31. The apparatus of claim 1, further comprising a final filter to collect particles exiting said apparatus.

32. The apparatus of claim 1, wherein said at least one sensor comprises at least one gas sensor.

33. (currently amended) The apparatus of claim 1, further comprising means for providing input to said microprocessor for noting a patient's temporal symptom occurrence, wherein said software includes means for analyzing said patient's temporal symptom occurrence with respect a time signature of said at least one particle to identify what particle caused a patient's reaction.

34. A method for detecting allergens and/or irritants, comprising:
    detecting with a sensor at least one type of particle selected from the group consisting of an allergen and an irritant, wherein said sensor is operatively connected to control electronics, wherein said sensor produces data when it detects said at least one type of particle; and
    communicating said data from said sensor to a microprocessor comprising software and memory for storing and analyzing said data.

35. The method of claim 34, wherein said software analyzes said data to produce analyzed data indicative of the quantity of said allergens and/or irritants.

36. The method of claim 35, further comprising displaying information selected from the group consisting of said data, said analyzed data, a menu and status of the apparatuses used in the method.

37. The method of claim 34, wherein said sensor is selected from the group consisting of a gas sensor, a temperature sensor, an optical sensor, a fluorescence sensor and an electrical impedance sensor.

38. The method of claim 34, wherein said at least one sensor is selected from the group consisting of an allergen sensor and an irritant sensor.

39. The method of claim 34, wherein said software comprises means for specifying the allergens and/or irritants and their levels to be measured.

40. The method of claim 34, further comprising generating a signal when the concentration of said at least one particle exceeds a predefined level.

41. The method of claim 34, wherein said data is communicated by wireless communication.

42. The method of claim 34, further comprising downloading information from portable respiratory testing device to quantify decrease in pulmonary function and correlate pulmonary function to the presence of an allergen and/or irritant.

* * * * *